(12) United States Patent
Xu et al.

(10) Patent No.: US 12,324,591 B2
(45) Date of Patent: Jun. 10, 2025

(54) OSTEOTOMY GUIDE

(71) Applicant: DePuy Synthes Products, Inc., Raynham, MA (US)

(72) Inventors: Qiang Xu, Suzhou (CN); Wenhao Qi, Suzhou (CN); Mingjun Zhang, Suzhou (CN); Weiwei Xiang, Suzhou (CN); Xiaolong Wang, Suzhou (CN)

(73) Assignee: DePuy Synthes Products, Inc., Raynham, MA (US)

( * ) Notice: Subject to any disclaimer, the term of this patent is extended or adjusted under 35 U.S.C. 154(b) by 540 days.

(21) Appl. No.: 17/602,430

(22) PCT Filed: Apr. 12, 2019

(86) PCT No.: PCT/CN2019/082425
§ 371 (c)(1),
(2) Date: Oct. 8, 2021

(87) PCT Pub. No.: WO2020/206674
PCT Pub. Date: Oct. 15, 2020

(65) Prior Publication Data
US 2022/0167992 A1   Jun. 2, 2022

(51) Int. Cl.
*A61B 17/15* (2006.01)
*A61B 17/17* (2006.01)

(52) U.S. Cl.
CPC .......... *A61B 17/151* (2013.01); *A61B 17/155* (2013.01); *A61B 17/157* (2013.01); *A61B 17/1764* (2013.01)

(58) Field of Classification Search
CPC ... A61B 17/151; A61B 17/155; A61B 17/157; A61B 17/1764
See application file for complete search history.

(56) References Cited

U.S. PATENT DOCUMENTS

| | | |
|---|---|---|
| 5,423,827 A | 6/1995 | Mumme et al. |
| 8,083,746 B2 | 12/2011 | Novak |
| 8,377,068 B2 | 2/2013 | Aker et al. |
| 11,399,849 B2 | 8/2022 | Podgorski et al. |
| 2006/0155291 A1 | 7/2006 | Farrar et al. |
| 2006/0241636 A1 | 10/2006 | Novak et al. |

(Continued)

FOREIGN PATENT DOCUMENTS

| | | |
|---|---|---|
| CN | 104736072 A | 6/2015 |
| CN | 104825214 A | 8/2015 |

(Continued)

*Primary Examiner* — Sameh R Boles
(74) *Attorney, Agent, or Firm* — BakerHostetler

(57) ABSTRACT

An osteotomy guide (100) includes an inner surface (102) that faces the bone (300), and an outer surface (104) opposite the inner surface (102) along an outward direction ($D_o$). The inner surface (102) defines proximal and distal bone contacting regions (118,120) that are spaced from one another by a gap (124) that extends into the inner surface (102) towards the outer surface (104). The guide (100) includes an ascending guide surface (134) that extends along an ascending direction so as to define an ascending cutting path into the bone (300). The guide (100) includes a transverse guide surface (138) that extends along a transverse direction so as to define a transverse cutting path into the bone (300).

20 Claims, 8 Drawing Sheets

(56) References Cited

U.S. PATENT DOCUMENTS

| | | |
|---|---|---|
| 2008/0015605 A1 | 1/2008 | Collazo |
| 2009/0087276 A1 | 4/2009 | Rose |
| 2012/0143199 A1 | 6/2012 | Young |
| 2014/0066720 A1* | 3/2014 | Wilkinson ............. A61B 17/02 606/88 |
| 2015/0305752 A1 | 10/2015 | Eash |
| 2016/0287298 A1 | 10/2016 | Pavlov et al. |
| 2017/0325826 A1 | 11/2017 | Bake et al. |
| 2017/0360453 A1 | 12/2017 | Brailovski et al. |
| 2018/0049749 A1 | 2/2018 | Wu et al. |
| 2019/0150943 A1 | 5/2019 | Wu et al. |
| 2019/0314038 A1 | 10/2019 | Maxson |

FOREIGN PATENT DOCUMENTS

| | | | |
|---|---|---|---|
| CN | 104825215 A | 8/2015 | |
| CN | 105193475 A | 12/2015 | |
| CN | 205339051 U | 6/2016 | |
| CN | 205359552 U | 7/2016 | |
| CN | 206333941 U | 7/2017 | |
| CN | 107072672 A | 8/2017 | |
| CN | 107320153 A | 11/2017 | |
| CN | 107753088 A | 3/2018 | |
| CN | 207532417 U | 6/2018 | |
| CN | 108618823 A | 10/2018 | |
| CN | 109512484 A | 3/2019 | |
| EP | 1444957 A1 | 8/2004 | |
| JP | 06-014947 A | 1/1994 | |
| JP | 2005-535426 A | 11/2005 | |
| JP | 2008-529607 A | 8/2008 | |
| JP | 2010-540123 A | 12/2010 | |
| JP | 2016-093736 A | 5/2016 | |
| JP | 2018-115316 A | 7/2018 | |
| JP | 2019-034120 A | 3/2019 | |
| JP | 2019202108 A * | 11/2019 | ........... A61B 17/025 |
| TW | I655926 B | 4/2019 | |
| WO | 2015/061917 A1 | 5/2015 | |
| WO | 2019/033551 A1 | 2/2019 | |
| WO | 2019/038240 A1 | 2/2019 | |

* cited by examiner

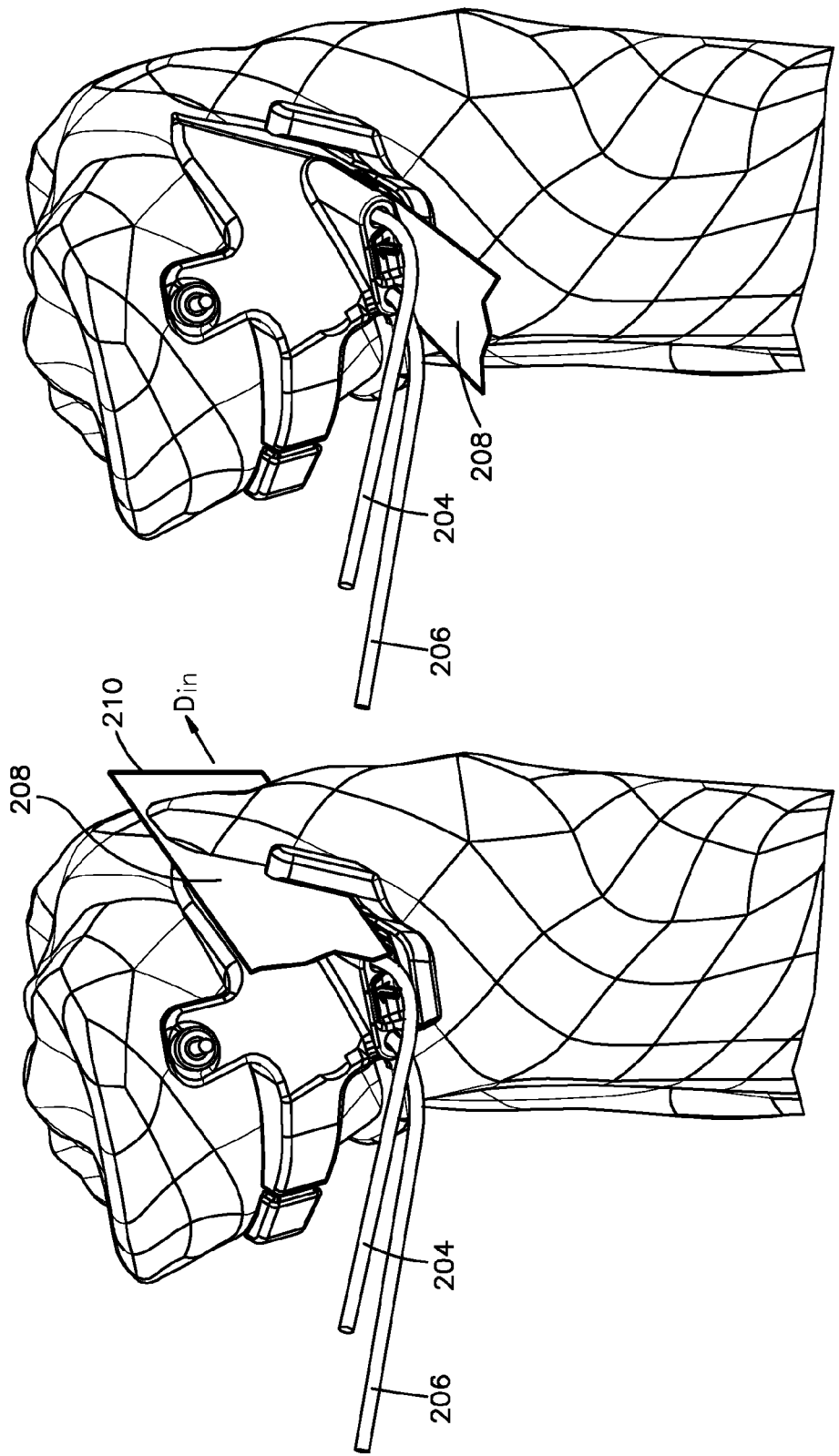

OSTEOTOMY GUIDE

CROSS-REFERENCE TO RELATED APPLICATIONS

This application is the National Stage of International Patent Application No. PCT/CN2019/082425, filed Apr. 12, 2019.

TECHNICAL FIELD

The present disclosure relates to a surgical guide for cutting bone during an osteotomy, and methods for using the same.

BACKGROUND

The cartilage in a joint, such as a knee, can wear down over time or become damaged due to an injury related to physical activity, resulting in osteoarthritis. Wearing of the cartilage can result in pain that limits the activity of daily life. Typically, osteoarthritis was treated by implanting an artificial joint to replace the original joint. However, there are several drawbacks to full joint replacements. For instance, joint replacements often require large portions of the articular surface of the joint to be removed to accommodate fixation of a metal or polymer joint implant. Further, replacement joints often have a limited life of up to twenty years, and therefore, subsequent replacement surgeries are often needed. Yet further, joint replacements are often complicated by postoperative infection, osteolysis, and osteoporosis, which may require an additional surgery.

Some patients with early onset of osteoarthritis experience cartilage wear of only a portion of the articular surface, such as cartilage wear of less than all of the compartments of the joint. For example, some patients may experience bi-compartmental osteoarthritis of two compartments of the joint or uni-compartmental osteoarthritis of a single compartment of the joint. For patients with compartmental osteoarthritis, it might not be necessary to remove and replace the entire articular surface. Therefore, an osteotomy, such as a high tibial osteotomy, can be performed in patients with limited cartilage wear. For example, a medial high-tibial osteotomy can be performed for patients with medial compartmental osteoarthritis to realign the knee joint.

A medial high-tibial osteotomy is performed by making a cut into the patient's tibia at a location that is adjacent the proximal end of the tibia and on the medial side. The proximal end of the patient's tibia is pivoted to enlarge the cut so as to realign the articular surface of the knee. The proximal end of the tibia can then be fixed in position so as to maintain the enlarged cut by attaching a bone plate to the tibia. The bone plate extends across the enlarged cut and is attached to the tibia on opposed sides of the cut. In some procedures, the cut can be filled with bone graft or artificial bone before or after the plate is attached.

SUMMARY

In an example embodiment, an osteotomy guide comprises an inner surface configured to face bone, and an outer surface opposite the inner surface along an outer direction. Each of the inner surface and the outer surface extends between an anterior end of the osteotomy guide and a posterior end of the osteotomy guide. The inner surface defines i) a proximal bone contacting region, and ii) a distal bone contacting region that is spaced from the proximal bone contacting region along a distal direction so as to define a gap. The gap extends along the distal direction from the proximal bone contacting region to the distal bone contacting region, and extends from the inner surface toward the outer surface along the outer direction. The osteotomy guide comprises at least one ascending guide surface that extends between the outer surface and the inner surface. The ascending guide is oriented along an ascending direction so as to at least partially define an ascending cutting path into the bone. The ascending direction is angularly offset from the distal direction and a posterior direction that is perpendicular to each of the distal direction and the outer direction. The osteotomy guide comprises at least one transverse guide surface that extends between the outer surface and the inner surface, and is oriented along a transverse direction so as to at least partially define a transverse cutting path into the bone that intersects the ascending cutting path. The transverse guide surface is offset from the gap along the distal direction.

In another embodiment, an osteotomy guide is configured to guide an osteotomy cut into a bone. The osteotomy guide comprises an inner surface configured to face the bone, and an outer surface that is opposite the inner surface. At least a portion of the inner surface is contoured to face the bone. The osteotomy guide comprises first and second ascending guide surfaces that face each other so as to define an ascending cutting path therebetween that extends along an ascending direction. The osteotomy guide comprises first and second transverse guide surfaces that face each other so as to define a transverse cutting path therebetween that intersects the ascending cutting path.

In yet another embodiment, an osteotomy guide comprises an inner surface configured to face bone, and an outer surface opposite the inner surface. Each of the inner surface and the outer surface extends between a posterior end of the osteotomy guide and an anterior end of the osteotomy guide. The inner surface is opposite the outer surface along an inner direction. The inner surface defines i) a proximal bone contacting region, ii) a distal bone contacting region that is spaced from the proximal bone contacting region along a distal direction, and iii) a third bone contacting region that extends between the proximal bone contacting region and the distal bone contacting region. The osteotomy guide defines a gap that 1) is at least partially defined by proximal bone contacting region, the distal bone contacting region, and the third bone contacting region, and 2) extends from the inner surface toward the outer surface along the inner direction, wherein the distal direction is perpendicular to the inner direction. The osteotomy guide comprises at least one ascending guide surface that extends between the outer surface and the inner surface, and is oriented along an ascending direction so as to at least partially define an ascending cutting path into the bone. The ascending direction is angularly offset from the distal direction and a posterior direction that is perpendicular to each of the distal direction and the inner direction. The osteotomy guide comprises at least one transverse guide surface that extends between the outer surface and the inner surface, and is oriented along a transverse direction so as to at least partially define a transverse cutting path into the bone that intersects the ascending cutting path direction.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

FIG. 13 shows a perspective view of the tibia, fibula, and osteotomy guide of FIG. 10 with a cutting instrument making an ascending cut in the bone;

FIG. 14 shows a perspective view of the tibia, fibula, and osteotomy guide of FIG. 10 with a cutting instrument making a transverse cut in the bone.

DETAILED DESCRIPTION OF ILLUSTRATIVE EMBODIMENTS

Figure 1:
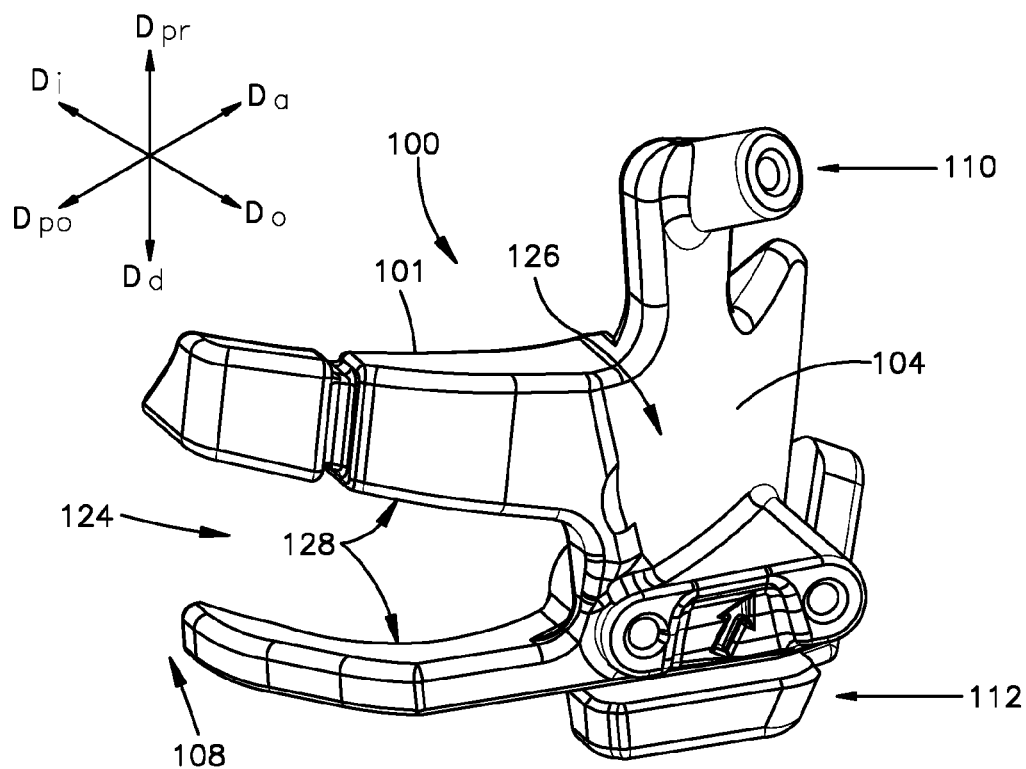
FIG. 1 shows an outer perspective view of an osteotomy guide according to one embodiment.
Figure 2:
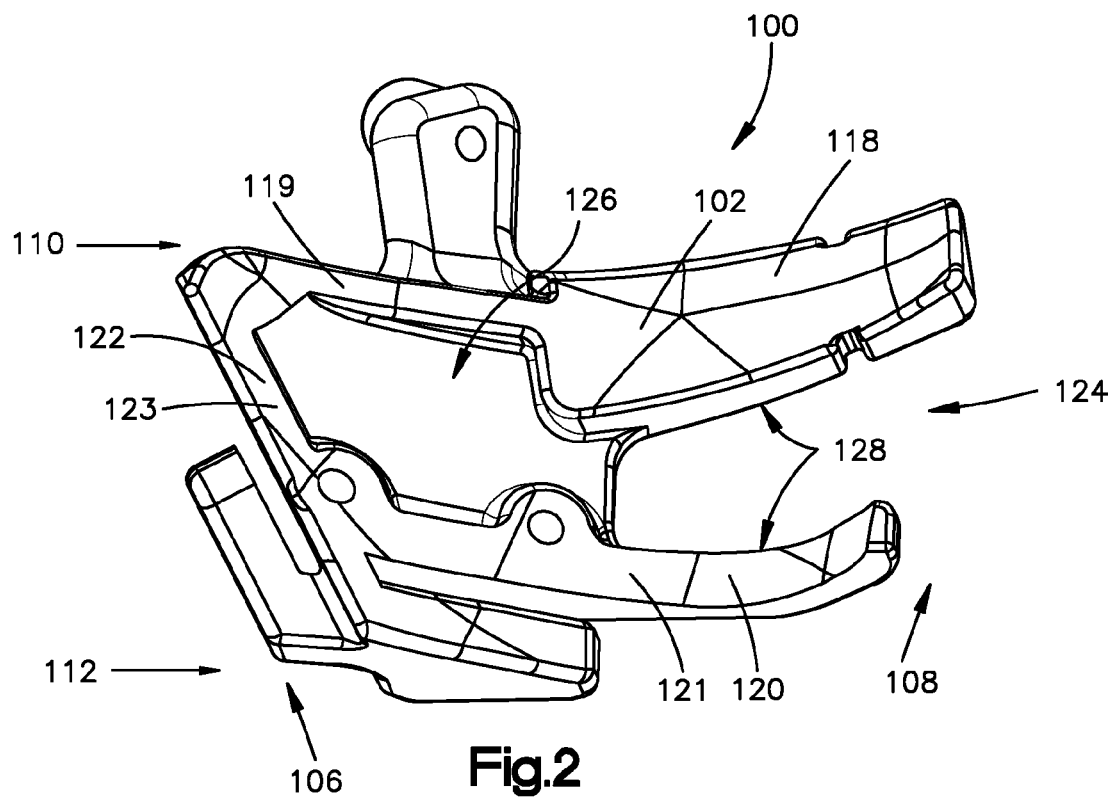
FIG. 2 shows an inner perspective view of the osteotomy guide of FIG. 1.

With general reference to FIGS. 1 to 8, an osteotomy guide is shown according to one embodiment. The osteotomy guide 100 is configured to guide at least one cutting instrument to make a cut into a bone for an osteotomy procedure. The osteotomy guide 100 can be custom constructed to conform to a bone of a specific patient. In other words, the osteotomy guide 100 may be patient specific. The osteotomy guide 100 can be three-dimensionally (3-D) printed or can be fabricated in any other suitable manner. In at least some embodiments, the osteotomy guide 100 can include a one-piece body. The osteotomy guide 100 defines at least one ascending guide surface 134 and at least one transverse guide surface 138 (both labeled in FIGS. 5 and 6) that are configured to guide at least one cutting instrument, such as a saw blade, to make a cut into a bone such as a tibia, femur, fibula, humerus, ulna, radius, or other bone. The osteotomy guide 100 can be configured to guide a cut into the bone adjacent to a joint. The cut can then be enlarged by pivoting a proximal end of the patient's bone so as to realign the articular surface of the joint. The enlarged cut can then be fixed by attaching a bone plate that extends across the cut and is attached to the bone on opposed sides of the enlarged cut. For illustrative purposes, the guide 100 will be described and shown relative to its use in making a cut in a tibia.

Referring more specifically to FIGS. 1-4, the osteotomy guide 100 has an inner surface 102, and an outer surface 104 opposite the inner surface 102 with respect to an outward direction $D_o$. In other words, the inner surface 102 is opposite from the outer surface 104 with respect to an inward direction $D_i$, where the inward direction $D_i$ is opposite the outward direction $D_o$. The inner surface 102 can be a bone-facing surface configured to face the bone. Preferably, the inner surface 102 is configured to contact the bone, and thus, can be considered to be a bone contacting surface. The inner surface 102 can be contoured so as to conform to a surface of the bone. The contour can be generally concave or can be any suitable contour to match the surface of the bone. The outer surface 104 can be configured to face away from the bone. In some examples, the outer surface 104 can be substantially convex, although embodiments of the disclosure are not so limited.

The osteotomy guide 100 has an anterior end 106, and a posterior end 108 opposite the anterior end 106 with respect to a posterior direction $D_{po}$. In other words, the anterior end 106 is opposite the posterior end 108 with respect to an anterior direction $D_a$, where the anterior direction $D_a$ and posterior direction $D_{po}$ are opposite one another. The osteotomy guide 100 can be configured to be positioned on the bone such that the anterior end 106 is adjacent an anterior side of the bone and the posterior end 108 is adjacent a posterior side of the bone. However, it will be understood that osteotomy guide 100 can be otherwise positioned. The anterior direction $D_a$ and the posterior direction $D_{po}$ can be perpendicular to both the inward and outward directions $D_{in}$ and $D_o$.

The osteotomy guide 100 has a proximal end 110, and a distal end 112 opposite the proximal end 110 with respect to a distal direction $D_d$. In other words, the proximal end 110 is opposite the distal end 112 with respect to a proximal direction $D_{pr}$, where the proximal direction $D_{pr}$ and distal direction $D_d$ are opposite one another. The osteotomy guide 100 is configured to be positioned on the bone such that the proximal end 110 is oriented towards a proximal side of the bone, and the posterior end 112 is oriented towards a distal end the bone. The proximal direction $D_{pr}$ and distal direction $D_d$ can be perpendicular to the inward direction $D_{in}$, the outward direction $D_o$, the anterior direction $D_a$, and the posterior direction $D_{po}$.

The inner surface 102, and thus osteotomy guide 100, has at least two bone contacting regions that are configured to contact the bone when the osteotomy guide 100 is positioned along the bone. Each bone contacting region can be specifically sized and shaped to a contour of the bone of a particular patient. The at least two bone contacting regions can include a first bone contacting region 118. The first bone contacting region 118 can be positioned closer to the proximal end 110 than a second bone contacting region 120 (discussed below). Thus, the first bone contacting region 118 may be considered to be a proximal bone contacting region. The first bone contacting region 118 can extend between the anterior end 106 and the posterior end 108. For example, the first bone contacting region 118 can be elongate as it extends between the anterior end 106 and the posterior end 108. In some embodiments, the first bone contacting region 118 can extend from the anterior end 106 to the posterior end 108. At least a portion, up to an entirety, of the first bone contacting region 118 can be contoured as it extends between the anterior end 106 to the posterior end 108 so as to conform to the bone. The contour can be generally concave or can be any suitable contour to match the surface of the bone. A posterior end, such as a free end, of the proximal bone contacting region 118 can be configured (e.g., sized and shaped) to hook the H point of the bone when the osteotomy guide 100 is affixed to the bone.

The at least two bone contacting regions can include a second bone contacting region 120. The second bone contacting region 120 can be offset from the proximal bone contacting region 118 along the distal direction $D_d$ so as to define a gap 124 therebetween. In other words, the proximal bone contacting region 118 can be offset from the distal bone contacting region 120 along the proximal direction $D_{pr}$ so as to define a gap 124 therebetween. The second bone contacting region 120 can be positioned closer to the distal end 112 than the first bone contacting region 118. Thus, the second bone contacting region 122 may be considered to be a distal bone contacting region. The second bone contacting region 120 can extend between the anterior end 106 and the posterior end 108. For example, the second bone contacting region 120 can be elongate as it extends between the anterior end 106 and the posterior end 108. In some embodiments, the distal bone contacting region 120 can extend from the anterior end 106 to the posterior end 108. At least a portion, up to an entirety, of the second bone contacting region 120 can be concave as it extends between the anterior end 106 to the posterior end 108 so as to conform to the bone. A posterior end, such as a free end, of the distal bone contacting region 120 can be configured (e.g., sized and shaped) to hook the posterior ridge of the bone when the osteotomy guide 100 is affixed to the bone.

In at least some embodiments, the at least one bone-facing surface can include a third bone contacting region 122. The third bone contacting region 122 can extend between the first bone contacting region 118 and the second bone contacting region 120. For example, the third bone contacting region 122 can extend from the first bone contacting region 118 to the second bone contacting region 120. The third bone contacting region 122 can be elongate as it extends between the first bone contacting region 118 and the second bone contacting region 120. The third bone contacting region 122 can be disposed at the anterior end 106 of the osteotomy guide 100. Thus, the third bone contacting region 122 can extend between the first bone contacting region 118 and the second bone contacting region 120 at the anterior end 106. Accordingly, the third bone contacting region 122 can be considered to be an anterior bone contacting region. The third bone contacting region 122 can be concave as it extends towards the posterior end 108. It will be understood that, in alternative embodiments, the osteotomy guide 100 can be implemented without the third bone contacting region 122 or the third bone-facing surface can extend between the first bone contacting region 118 and the second bone contacting region 120 at a location that is offset from the anterior end 106.

The at least two bone contacting regions can provide a better fit on the bone than one larger bone contacting surface. For example, the gap 124 between the first bone contacting region 118 and the second bone contacting region 120 can provide space for bony protrusions to extend between the first bone contacting region 118 and the second bone contacting region 120.

The osteotomy guide 100 can include an anterior body portion 126, and a posterior body portion 128 that is offset from the anterior body portion 126 along the posterior direction $D_{po}$. The anterior body portion 126 can at least partially define the anterior end 106 and can extend from the anterior end 106 towards the posterior end 108. The posterior body portion 128 can at least partially define the posterior end 108 and can extend from the posterior end 108 towards the anterior end 106. The osteotomy guide 100 can include a proximal wall 119 that defines the proximal bone contacting region 118. The osteotomy guide 100 can include a distal wall 121 that defines the distal bone contacting region 120. The distal wall 121 can be spaced from the proximal wall 119 along the distal direction $D_d$ so as to define the gap 124 therebetween. The anterior body portion 126, and hence the osteotomy guide 100, can include a third wall 123 that defines the third bone contacting region 122. The third wall 123 can extend between the proximal wall 119 and the distal wall 121, such as from the proximal wall 119 to the distal wall 121. The gap 124 can extend into the posterior end 108 towards the anterior end 106 such that the gap 124 is open at the posterior end 124. The gap 124 can extend towards and terminate at, for example, the third bone contacting region 122, such as at the third wall 123 that defines the third bone contacting region 122. It will be understood that, in some embodiments, the gap 124 can be closed at the posterior end 124.

The gap 124 extends into the inner surface 102 towards the outer surface 104. At least a portion of the gap 124 can extend through the outer surface 104. For example, the gap 124 can extend through the outer surface 104 at the posterior body portion 128. In other words, at least a portion, such as an anterior portion, of the gap 124 can be open at the inner surface 102 and the outer surface 104. At least a portion of the gap 124 can terminate at the outer surface 104. For example, the gap 124 can terminate at the outer surface 104 at the anterior body portion 126. Thus, at least a portion, such as an anterior portion, of the gap 124 can be open at the inner surface 102 and closed at the outer surface 104. It will be understood that, in some embodiments, the anterior portion of the gap 124 can be open at the outer surface 104. Additionally, or alternatively, in some embodiments, the posterior portion of the gap 124 can be closed at the outer surface 104. In some embodiments, the gap 124 can have a dimension along the proximal direction $D_{pr}$ or distal direction $D_d$ that is greater than, or equal to, a dimension of at least one, such as both, of the proximal bone contacting region 118 and the distal bone contacting region 118 along the same direction.

Referring to FIGS. 5 to 8, in embodiments where the gap 124 extends through the inner surface 102 and the outer surface 104, the posterior body portion 128, and thus osteotomy guide 100, can include a proximal arm 130, and a distal arm 132 that is offset from the proximal arm 130 with respect to the distal direction $D_d$. The proximal arm 130 and the distal arm 132 can be separated from one another by the gap 124. The proximal arm 130 can extend from the anterior body portion 126 towards the posterior end 108. Thus, the proximal arm 130 can have a first end that is attached to the anterior body portion 126 and a second end that is spaced from the first end along the posterior direction $D_{po}$. The second end can be a free end of the proximal arm 130. Similarly, the distal arm 132 can extend from the anterior body portion 126 towards the posterior end 108. Thus, the distal arm 132 can have a first end that is attached to the anterior body portion 126 and a second end that is spaced from the first end along the posterior direction $D_{po}$. The second end can be a free end of the distal arm 132. In some embodiments, the proximal arm 130 can be angled away from the distal arm 132 as the proximal arm 130 extends towards the posterior end 108. It will be understood that the precise shape of each of the first and second arm may vary based on the specific curvatures of the patient's bone.

Figure 3:
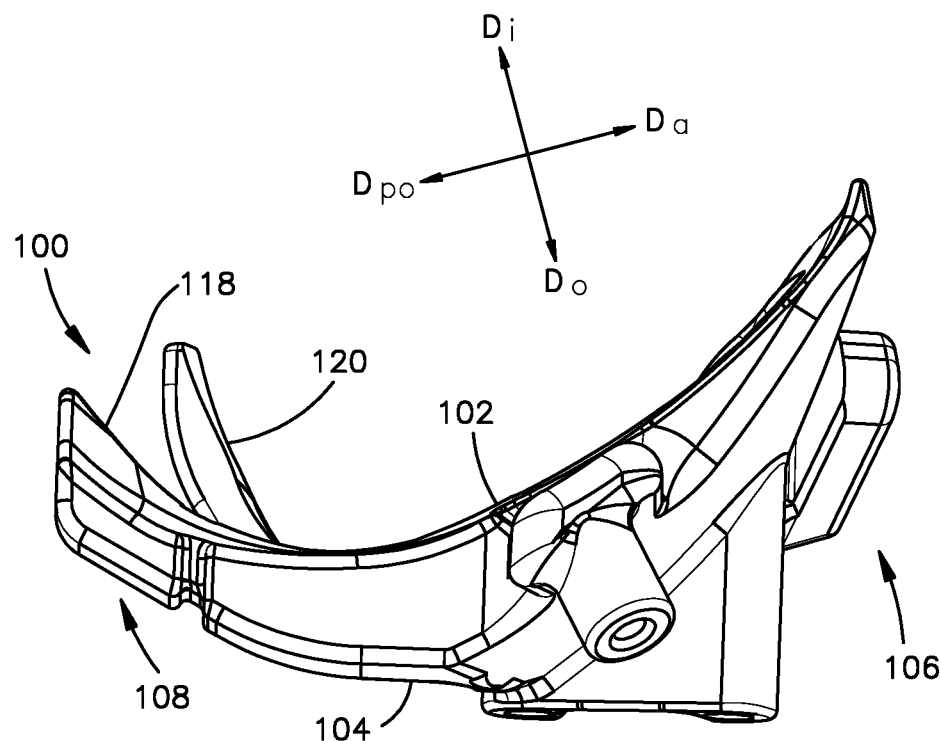
FIG. 3 shows plan view of a proximal end of the osteotomy guide of FIG. 1.
Figure 4:
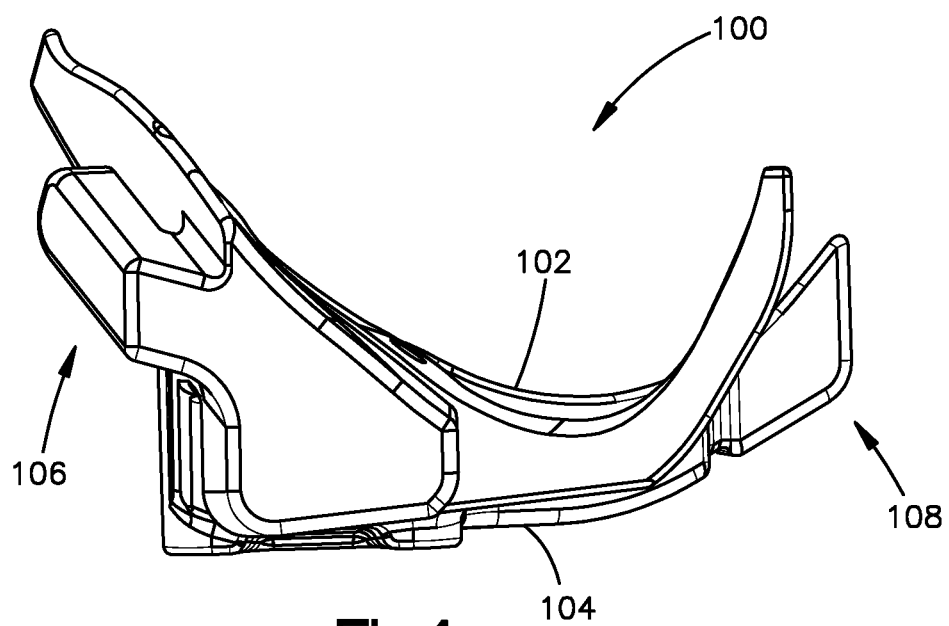
FIG. 4 shows plan view of a distal end of the osteotomy guide of FIG. 1.

The proximal arm 130 can include at least a portion, such as a posterior portion, of the proximal bone contacting region 118. The distal arm 132 can include at least a portion, such as a posterior portion, of the distal bone contacting region 120. The proximal bone contacting region 118 has a first curvature, and the distal bone contacting region 120 has a second curvature that is different from the first curvature. For example, the second curvature can be greater than the first curvature. Thus, the distal bone contacting region 120 can curve further inward than the proximal bone contacting region 118 as can be seen in FIG. 3. It will be understood that, in alternative embodiments, the first and second curvatures may be different from that shown and may vary based on the curvatures of a particular patient's bone.

Figure 5:
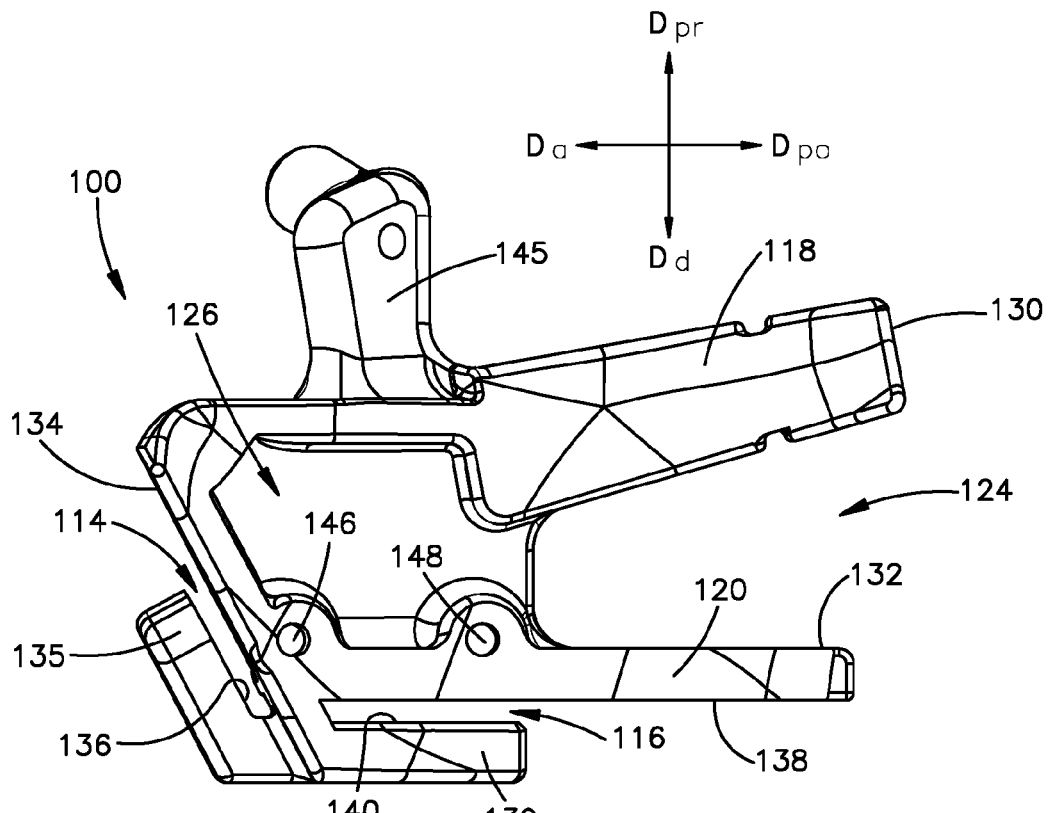
FIG. 5 shows elevation view of an inner side of the osteotomy guide of FIG. 1.
Figure 6:
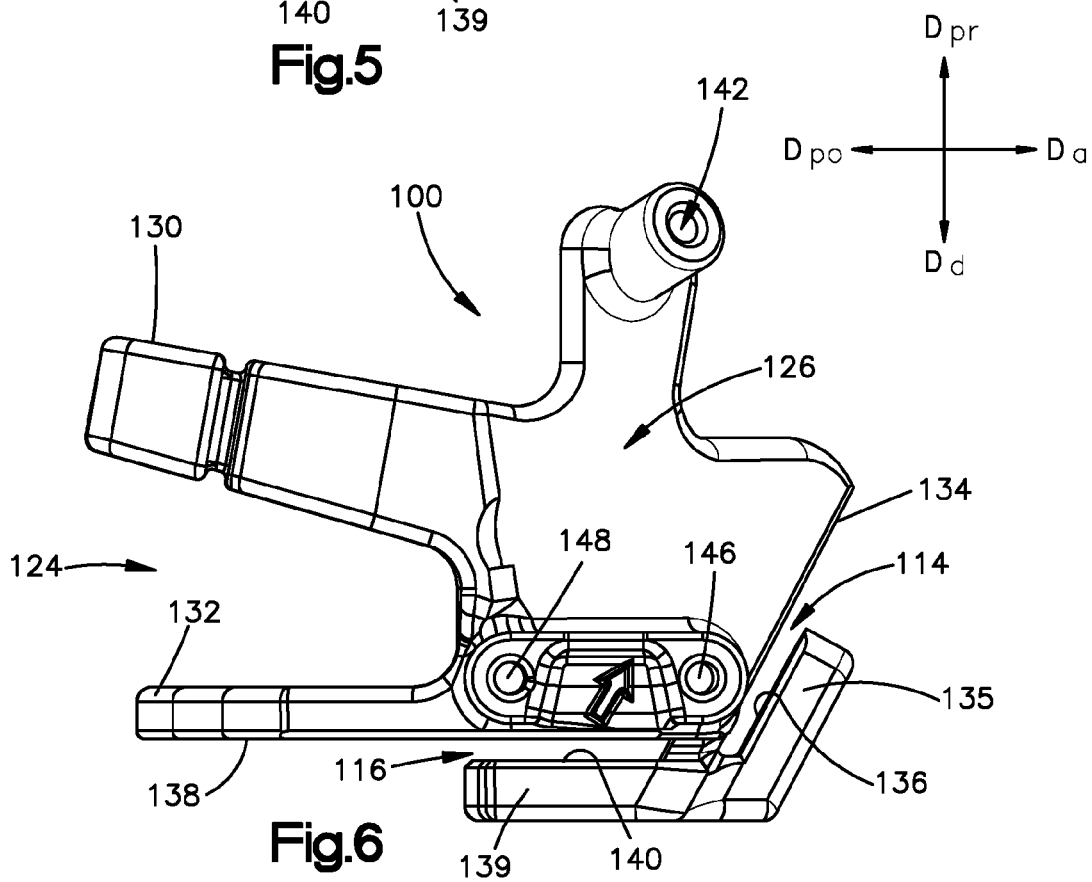
FIG. 6 shows elevation view of an outer side of the osteotomy guide of FIG. 1.
Figure 7:
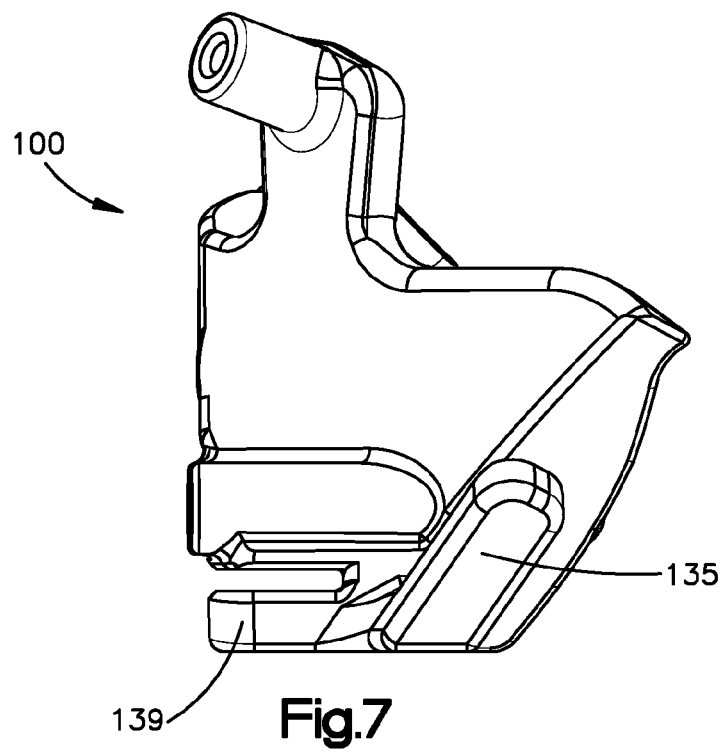
FIG. 7 shows elevation view of an anterior end of the osteotomy guide of FIG. 1.
Figure 8:
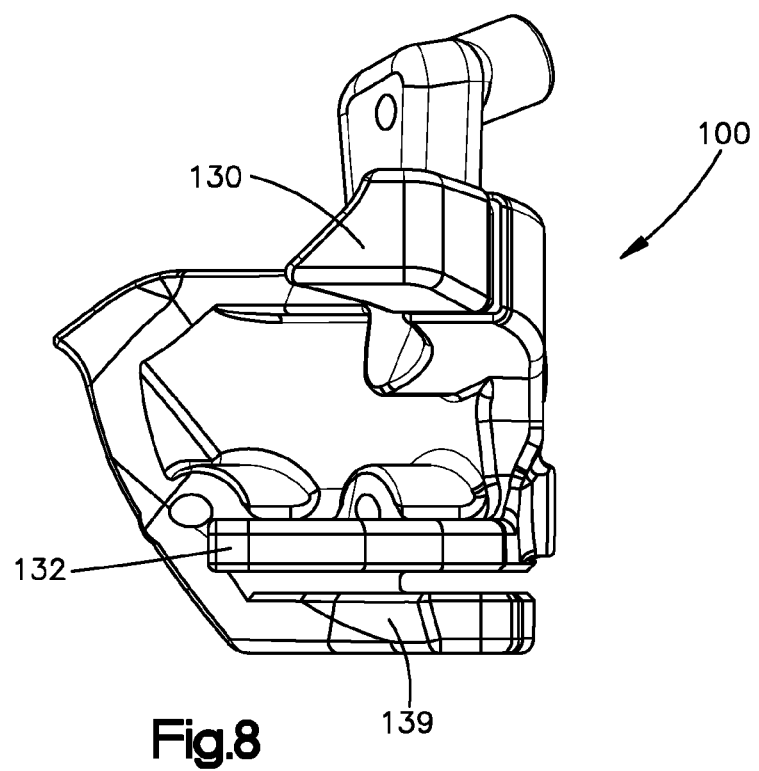
FIG. 8 shows elevation view of a posterior end of the osteotomy guide of FIG. 1.
Figure 10:
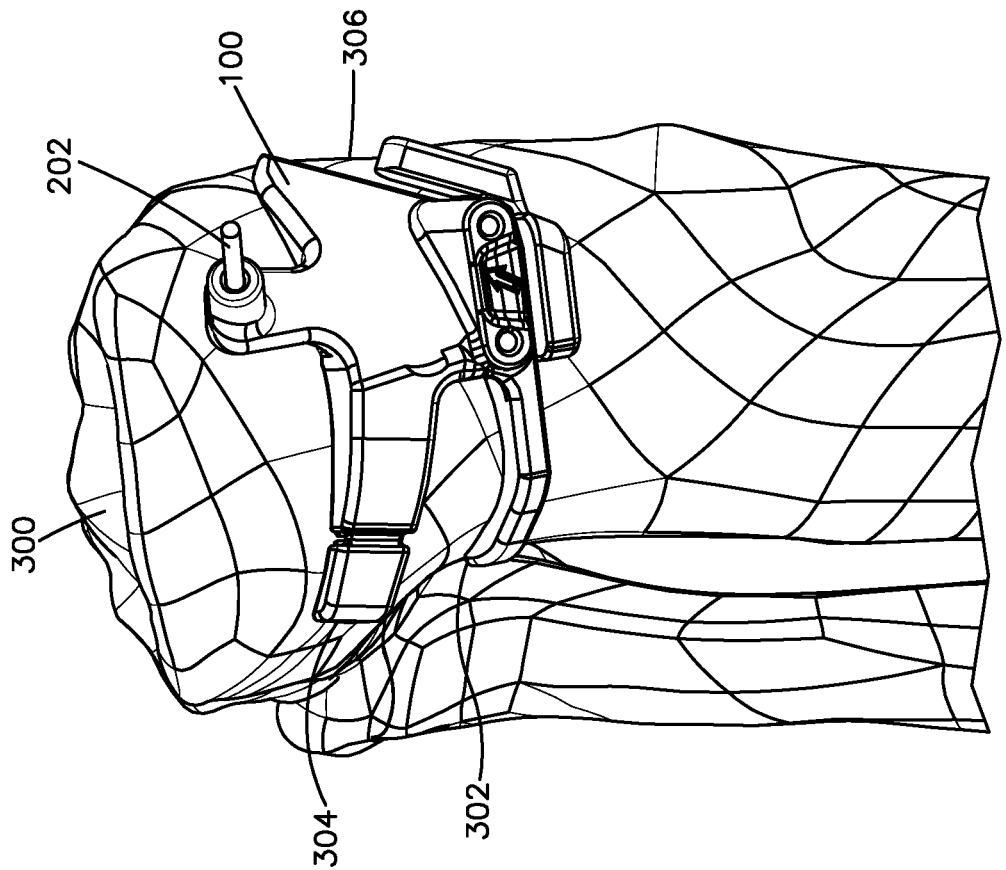
FIG. 10 shows a perspective view of a tibia and fibula along the lateral direction with the osteotomy guide of FIG. 1 attached to the tibia.
Figure 9:
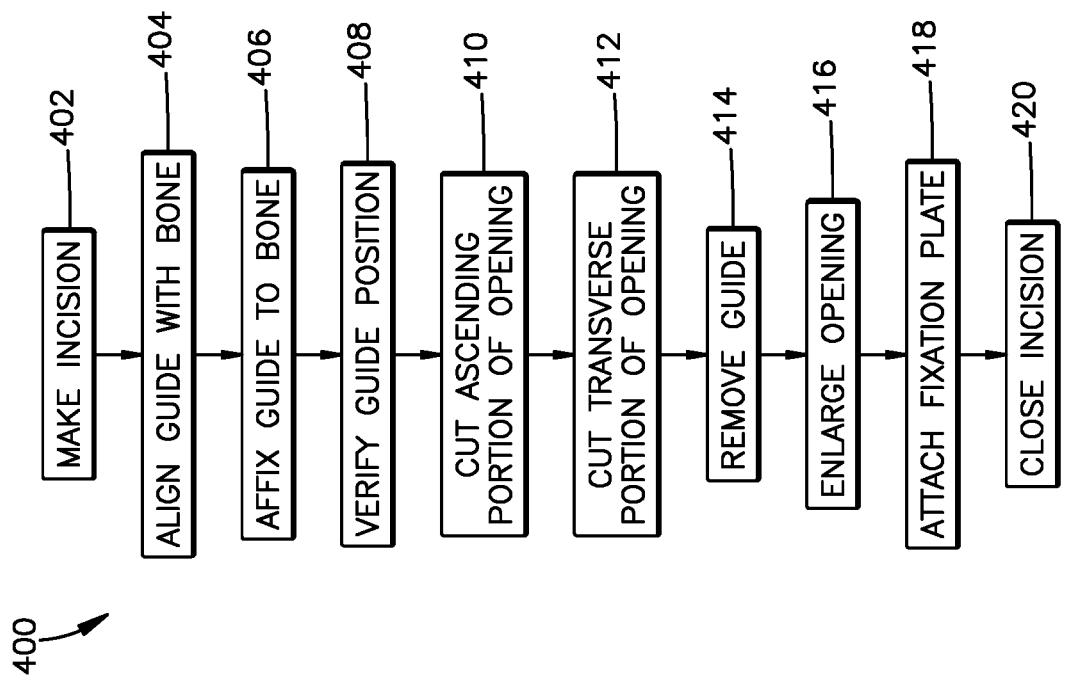
FIG. 9 shows a simplified block diagram of a surgical method according to one embodiment.
Figure 12:
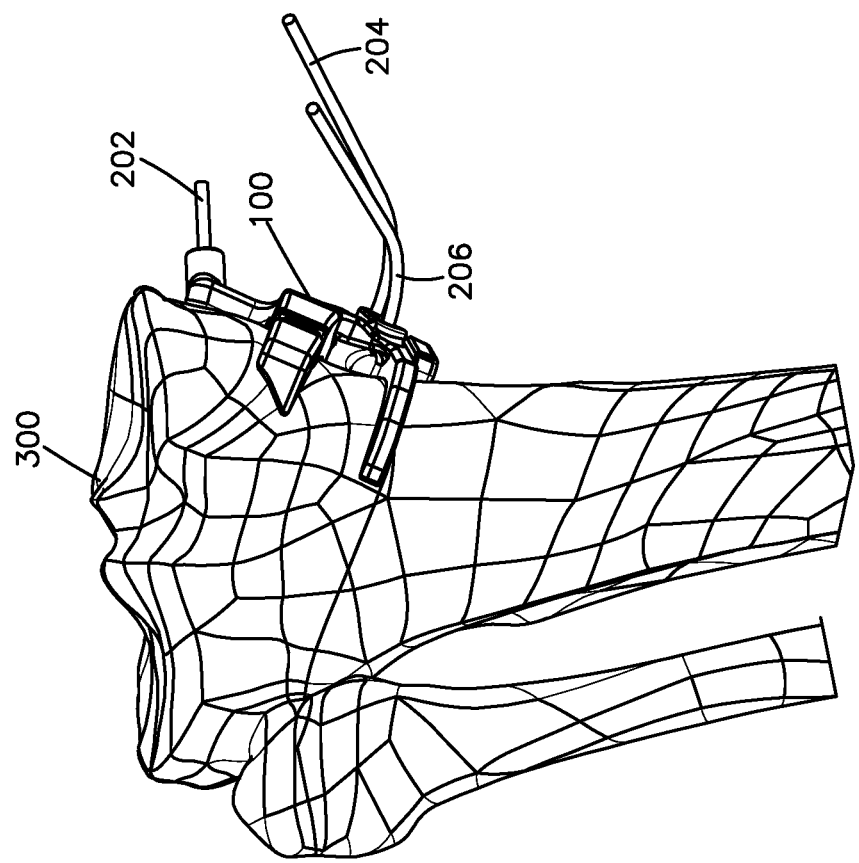
FIG. 12 shows a perspective view of the tibia, fibula, and osteotomy guide of FIG. 10 along the anterior direction.

With continued reference to FIGS. 5 and 6, the osteotomy guide 100 can have at least one ascending guide surface that is configured to guide the cutting instrument to make an ascending cut into the bone. The ascending cut may be made, for example, around the tibial tuberosity behind the patellar tendon. Thus, the osteotomy guide 100 can be configured (e.g., sized and shaped) such that each of the at least one ascending guide surface is aligned with the tibial tuberosity when the osteotomy guide 100 is affixed to the bone. Each of the at least one ascending guide surface can be disposed at the anterior end 106 of the osteotomy guide 100. The at least one ascending guide surface can include a first ascending guide surface 134. The first ascending guide surface 134 can extend along an ascending direction that is angularly offset with respect to the proximal direction $D_{pr}$ and the posterior direction $D_{po}$. For example, the ascending direction can extend at an angle that is between the proximal direction $D_{pr}$ and the posterior direction $D_{po}$. Thus, the first ascending guide surface 134 can be angled towards the anterior direction $D_a$ as the first ascending guide surface 134 extends towards the proximal end 110. The third wall 123 can define the first ascending guide surface 134.

In some embodiments, the at least one ascending guide surface can include a second ascending guide surface 136 that is offset from the first ascending guide surface 134 so as to define an ascending groove 114 therebetween. The second ascending guide surface 136 can extend along the ascending direction so as to at least partially define an ascending cutting path into the bone. Thus, the second ascending guide surface 136 can be angled towards the anterior direction $D_a$ as the second ascending guide surface 134 extends towards the proximal end 110. At least a portion of the first ascending guide surface 134 can face the second ascending guide surface 136 so as to define the ascending groove 114 therebetween. The ascending groove 114 can be configured to guide a cutting instrument to make an ascending cut into the bone. In some embodiments, the second ascending guide surface 136 can be substantially parallel to the first ascending guide surface 134. The first ascending guide surface 134 can have a length along the ascending direction that is greater than that of the second ascending guide surface 136, although embodiments of the disclosure are not so limited.

In embodiments having the second ascending guide surface 136, the osteotomy guide 100 can include an ascending leg 135 that defines the second ascending guide surface 136. The ascending leg 135 can have a first end that is attached to the anterior body portion 126, and a second end that is offset from the first end along the ascending direction. The ascending leg 135 can be integral and monolithic with the anterior body portion 126. The second end can be a free end that is free from attachment to the anterior body portion 126 or any other portion of osteotomy guide 100. The ascending groove 114 can extend into osteotomy guide 100 along a descending direction opposite the ascending direction. As such, a proximal end of the ascending groove 114 can be open, and a distal end of the ascending groove 114 can be closed, where the distal end is offset from the proximal end along the descending direction. It will be understood that, in alternative embodiments, the ascending groove 114 can terminate adjacent to the first end or can be open at both the first and second ends.

The osteotomy guide 100 can have at least one transverse guide surface that is configured to guide a cutting instrument to make a transverse cut into the bone. Each transverse guide surface can be disposed at the distal end 112 of the osteotomy guide 100. Each transverse guide surface can be offset from the gap 124 with respect to the distal direction $D_o$. For example, each transverse guide surface can be offset from the distal bone contacting region 120 with respect to the distal direction $D_o$. The at least one transverse guide surface can include a first transverse guide surface 138. The first transverse guide surface 138 can extend along the anterior direction $D_a$ and the posterior direction $D_{po}$ so as to at least partially define a transverse cutting path into the bone. The transverse cutting path can intersect the ascending cutting path.

In some embodiments, the at least one transverse guide surface can include a second transverse guide surface 140 that is offset from the first transverse guide surface 138 so as to define a transverse groove 116 therebetween. The second transverse guide surface 140 can extend along the anterior direction $D_a$ and the posterior direction $D_{po}$. At least a portion of the first transverse guide surface 138 can face the second transverse guide surface 140 so as to define the transverse groove 116 therebetween. The transverse groove 116 can be configured to guide a cutting instrument to make a transverse cut into the bone. The cutting instrument may be the same as, or different from, the cutting instrument used to make the ascending cut. In some embodiments, the second transverse guide surface 140 can be substantially parallel to the first transverse guide surface 138. The first transverse guide surface 138 can have a length along the posterior direction $D_{po}$ that is greater than that of the second transverse guide surface 140, although embodiments of the disclosure are not so limited.

In embodiments having the second transverse guide surface 140, osteotomy guide 100 can include a transverse leg 139 that defines the second transverse guide surface 140. The transverse leg 139 can have a first end that is attached to the anterior body portion 126, and a second end that is offset from the first end along the posterior direction $D_{po}$. The transverse leg 139 can be integral and monolithic with the anterior body portion 126. The second end can be a free end that is free from attachment to the anterior body portion 126 or any other portion of the osteotomy guide 100. The transverse groove 116 can extend into the osteotomy guide 100 along the anterior direction. As such, a posterior end of the transverse groove 116 can be open, and a posterior end of the transverse groove 116 can be closed, where the posterior end is offset from the anterior end along the posterior direction $D_{po}$. It will be understood that, in alternative embodiments, the transverse groove 116 can terminate adjacent to the first end or can be open at both the first and second ends.

The osteotomy guide 100 can define at least one fixation hole that extends through the osteotomy guide 100. Each fixation hole can be configured to receive a fixation pin, such as a Kirschner wire, therethrough so as to affix the osteotomy guide 100 to the bone. Each fixation hole can extend through the inner surface 102 and the outer surface 104 of the osteotomy guide 100. It will be understood that the locations of the fixation holes can vary from the embodiment shown.

In one example, the at least one fixation hole can include a proximal fixation hole 142 that is offset from the proximal bone contacting region 118 with respect to the proximal direction $D_{pr}$. The osteotomy guide 100 can include a neck 144 that extends from the anterior body portion 126 along the proximal direction $D_{pr}$. The proximal fixation hole 142 can extend through the neck 144. The neck 144 can have an inner surface 145 that is configured to face the bone. The inner surface 145 of the neck 144 can be offset with respect to the proximal bone-facing surface with respect to the outward direction $D_O$. Consequently, when the proximal bone-facing surface is aligned with the bone, the inner surface 145 of the neck 144 can be spaced from the bone so as to accommodate soft tissue between the inner surface 145 and the bone. Further, the proximal fixation hole 142 can correspond to a location of a hole of the bone fixation plate that is to be affixed to the bone. Thus, proximal fixation hole 142 can act as a guide for forming a hole in the bone that is used for both (i) a fixation pin that secures the osteotomy guide 100 to the bone and (ii) a bone anchor that affixes the bone fixation plate to the bone after the cut in the bone has been enlarged.

The at least one fixation hole can include at least one, such as two, distal bone fixation holes 146 and 148. Each distal bone fixation hole 146 and 148 can be offset from the proximal bone-fixation hole 142 with respect to the distal direction $D_d$. Each distal bone fixation hole 146 and 148 can extend through the anterior body portion 126 of the osteotomy guide 100. In embodiments having first and second distal bone fixation holes 146 and 148, the first distal bone fixation hole 146 can be spaced from the second distal bone fixation hole 148 along the anterior direction $D_a$. The first and second distal bone fixation holes 146 and 148 can be aligned along a direction that is substantially parallel with the at least one transverse guide surface 138.

The osteotomy guide 100 can be a unitary body having the anterior body portion 126, the proximal arm 130, the distal arm 132, the ascending leg 135, and the transverse leg 139. For example, the anterior body portion 126, the proximal arm 130, the distal arm 132, the ascending leg 135, and the transverse leg 139 can be integral and monolithic with one another. In one such example, the osteotomy guide 100 can be 3-D printed as a single monolithic body. Forming the osteotomy guide 100 as a single monolithic body can limit costs of 3-D printing the osteotomy guide 100 and can simplify the manufacturing process. In alternative embodiments, one or more of the proximal arm 130, the distal arm 132, the ascending leg 135, and the transverse leg 139 can be affixed, such as glued, welded, fastened, or otherwise coupled to, the anterior body portion 126. Providing the osteotomy guide 100 as a unitary body can simplify handling of the osteotomy guide 100 and improve cutting accuracy over conventional guides that include two or more movable parts where stability of the movable parts can be difficult to maintain.

In one embodiment, a method of fabricating the osteotomy guide 100 can include obtaining a 3-D computer model of the patient's anatomy. This obtaining step can comprise receiving the 3-D computer model in a computer. Additionally, or alternatively, this obtaining step can comprise obtaining an image of the patient's anatomy using an imaging machine, and generating the 3-D computer model of the patient's anatomy from the image. The method can comprise a step of generating a 3-D computer model of the osteotomy guide 100 that conforms to the patient's anatomy. The method can comprise a step of 3-D printing the osteotomy guide 100 based on the 3-D computer model of the osteotomy guide 100.

Figure 11:
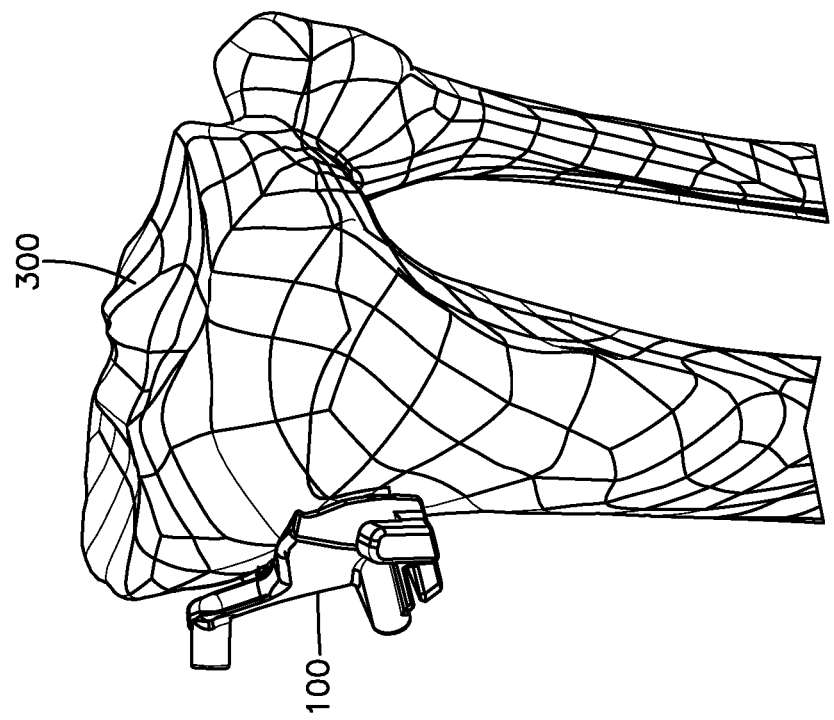
FIG. 11 shows a perspective view of the tibia, fibula, and osteotomy guide of FIG. 10 along the posterior direction.

Turning now to FIGS. 9 to 14, a surgical method 300 will now be described. It will be understood that various steps of the surgical method can be performed by different healthcare professionals. Accordingly, the surgical method can be divided into various sub-methods that can be performed separately of one another. The method can comprise an incision step 402 that comprises making an incision in the patient to access the patient's bone 300. The method can comprise an alignment step 404 that comprises aligning the osteotomy guide 100 onto the bone 300. For example, the alignment step 304 can comprise hooking the posterior end (e.g., free end) of the distal bone contacting region 120 around the H point 302 of the bone 300. The alignment step 304 can comprise hooking the posterior end (e.g., free end) of the distal bone contacting region 120 around the posterior ridge 304 of the bone 300. The alignment step 304 can comprise aligning the at least one ascending guide surface 134 and/or groove 114 with the tibial tuberosity 306. When the proximal bone-facing surface is aligned with the bone 300, the inner surface 145 of the neck 144 can be spaced from the bone 300 as shown in FIG. 11 so as to accommodate soft tissue between the inner surface 145 and the bone 300.

With the osteotomy guide 100 aligned, the osteotomy guide 100 can be affixed to the bone 300 in step 406. The affixation stem 406 can comprises inserting a fixation pin, such as a Kirschner wire, through at least one fixation hole in the osteotomy guide and into the bone. For example, the fixation step 406 can comprise inserting a fixation pin 202 through at least one proximal fixation hole 142 and into the bone 300. The fixation step 406 can comprise inserting a fixation pin through at least one distal fixation hole and into the bone 300. For example, the fixation step 406 can comprise inserting a fixation pin 204 through the first distal fixation hole 146 and into the bone 300. The fixation step 408 can comprise inserting a fixation pin 206 through a second distal fixation hole 148 and into the bone 300.

The method 400 can comprise a step 408 of verifying that the osteotomy guide 100 is positioned correctly. The verifying step 408 can comprise using x-ray for fluoroscopy to verify the position of the osteotomy guide 100. The method 400 comprises making the ascending portion 308 (labeled in FIG. 15) of the cut 307 into the bone (step 410) as shown in FIG. 13, and making the transverse portion 310 (labeled in FIG. 15) of the cut 307 into the bone 300 (step 412) as shown in FIG. 14. Step 410 can be performed before or after step 412. The ascending cut 308 and the transverse cut 310 can be each made with a cutting instrument such as a saw blade 208, and can be made with the same cutting instrument or with different cutting instruments. In one embodiment, the saw blade 208 can have a proximal end (not shown) that attaches to the saw, and a distal end 210 that is offset from the saw along an insertion direction $D_{in}$. The saw blade 208 can be elongate from its proximal end to its distal end 210, and can have a cutting edge at its distal end 210. The saw can oscillate the blade 208 along a direction that is perpendicular to the insertion direction $D_{in}$, and can cut into the bone 300 along the insertion direction $D_{in}$. The depth of the saw blade 208 can be controlled using depth markings on the saw blade 208, using a stop attached to the saw blade 208, or using any other suitable technique. To accommodate the cutting instrument, the at least one distal fixation pin 204 and 206 can be bent out of the path of the cutting instrument as shown in FIGS. 13 and 14. The bend of the fixation pins 204 and 206 can further secure the osteotomy guide 100 to the bone 300.

Figure 15:
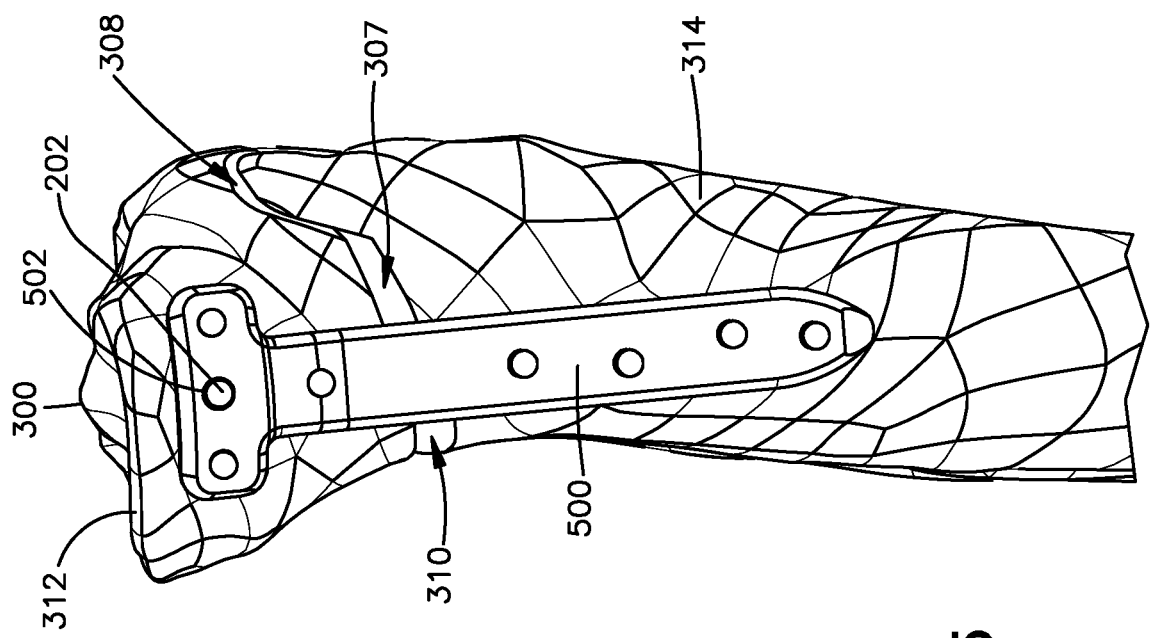
FIG. 15 shows an anterior view of the tibia and fibula of FIG. 10 after a cut has been formed in the tibia and a fixation plate has been attached to the tibia.

With specific reference to FIGS. 11 and 15, the method can comprise, after cutting the bone 300, a step 414 of removing the osteotomy guide 100. Step 414 can comprise removing the at least one distal fixation pin 204 and 206 before or after removing the osteotomy guide 100. The proximal fixation pin 202 can optionally be left in place. After removing the osteotomy guide 100, the method can comprise enlarging the cut 307 in the bone so at to realign the articular surface of the joint. The enlarging step 414 can comprise using a cutting instrument, such as a chisel or saw, to further enlarge the cut 307 so as to enable a proximal portion 312 of the bone 302 to pivot relative to a distal portion of the bone 314, where the proximal and distal portions 312 and 314 of the bone 300 are separated by the cut 307. For example, when cutting the ascending portion 308 and the transverse portion 310 of the cut 307, the cut might not be made through the portion of osteotomy guide 100 that closes the ascending groove 114 and the transverse groove 116 (i.e., that attaches the arms 135 and 139 to the anterior body portion 126). Therefore, after the osteotomy guide 100 is removed, a cutting instrument can be used to extend the transverse portion 310 of the cut 307 to the ascending portion 308 of the cut 307. The enlarging step 414 can comprise inserting wedges (not shown) or other instruments into the cut 307 so as to achieve a desired correction angle of the articular surface of the joint.

After enlarging the cut 307, a fixation plate 500 can be affixed to the proximal portion 312 and the distal portion 314 of the bone 300 in step 418 so as to maintain the cut 307 in the enlarged position. In one embodiment, step 418 can comprise aligning the fixation plate 500 with the bone 300 by receiving a fixation hole 502 of the bone plate 500 over the proximal fixation pin 202 (if the fixation pin 202 were left in place as described above). The fixation plate 500 can be affixed to the bone 300 by inserting bone anchors through the fixation plate 500 and into the proximal portion 312 and distal portion 314 of the bone 300. In step 420, the incision can be closed.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

What is claimed:

1. An osteotomy guide, comprising:
   a body that defines an inner surface configured to face bone, and an outer surface opposite the inner surface along an outer direction, wherein each of the inner surface and the outer surface extends between an anterior end of the osteotomy guide and a posterior end of the osteotomy guide, and the inner surface defines:
   i) a first arm that projects out from the body and defines a first bone-contacting surface; and
   ii) a second arm that projects out from the body and defines a second bone-contacting surface, wherein the second arm is spaced from the first arm along a first direction so as to define a gap that 1) extends along the first direction from the first arm to the second arm, and 2) extends entirely through the osteotomy guide from the inner surface toward the outer surface, wherein the first direction is perpendicular to the outer direction;
   first and second ascending guide surfaces that extend between the outer surface and the inner surface, and face each other so as to define an ascending groove that is elongate along an ascending direction so as to at least partially define an ascending cutting path into the bone, wherein the ascending direction is angularly offset from each of the first direction and a second direction that is perpendicular to each of the first direction and the outer direction; and
   first and second transverse guide surfaces that extend between the outer surface and the inner surface, and face each other so as to define a transverse groove that is elongate along a transverse direction so as to at least partially define a transverse cutting path into the bone that intersects the ascending cutting path, wherein the transverse groove defines an open end and a closed end that is opposite the open end along an inner transverse direction of the transverse direction, wherein the inner transverse direction and the ascending direction define an obtuse angle that is measured from one of the first and second ascending guide surfaces to one of the first and second transverse guide surfaces,
   wherein a portion of the body is disposed between the ascending groove and the transverse groove so as to separate the ascending groove from the transverse groove, such that one end of the ascending groove terminates at the portion of the body.

2. The osteotomy guide of claim 1, comprising an ascending leg having a first end that is attached to an anterior portion of the osteotomy guide, and a free end that is offset from the first end along the ascending direction, the ascending leg defining the second ascending guide surface.

3. The osteotomy guide of claim 1, wherein the ascending groove extends into the osteotomy guide along a descending direction, opposite the ascending direction, such that a proximal end of the ascending groove is open, and a distal end of the ascending groove is closed by the portion of the body.

4. The osteotomy guide of claim 1, wherein the osteotomy guide comprises an anterior body portion, and a transverse leg having a first end that is attached to the anterior body portion, and a free end that is offset from the first end along a posterior direction, the transverse leg defining the second transverse guide surface.

5. The osteotomy guide of claim 4, wherein the transverse groove extends into the osteotomy guide along an anterior direction, opposite the posterior direction, such that a posterior end of the transverse groove is open, and an anterior end of the transverse groove is closed.

6. The osteotomy guide of claim 1, comprising a third bone-facing surface that extends between the first and second arms.

7. The osteotomy guide of claim 6, wherein the gap extends into the posterior end and terminates at the third bone-facing surface.

8. The osteotomy guide of claim 1, comprising:
an anterior body portion, wherein
the first arm is a proximal arm that extends from the anterior body portion along a posterior direction; and
the second arm is a distal arm that extends from the anterior body portion along the posterior direction.

9. The osteotomy guide of claim 1, further comprising first and second bone fixation holes that are both spaced from each other along the transverse direction and aligned with each other along the transverse direction.

10. The osteotomy guide of claim 1, wherein the ascending groove defines an ascending plane that extends along the ascending direction and the outer direction, and the ascending plane is offset in its entirety from the gap.

11. An osteotomy guide configured to guide an osteotomy cut into a bone, the osteotomy guide comprising:
a body portion that defines an inner surface configured to face the bone, and an outer surface that is opposite the inner surface, wherein at least a portion of the inner surface is contoured to face the bone;
first and second ascending guide surfaces that face each other so as to define an ascending cutting path therebetween that extends along an ascending direction;
first and second transverse guide surfaces that face each other so as to define a transverse cutting path therebetween that intersects the ascending cutting path; and
first and second arms that project out from the body portion and define first and second bone contacting regions, respectively, wherein the first and second arms define a gap therebetween having 1) a first portion that extends entirely through the osteotomy guide and separates the first bone contacting region from the second bone contacting region, and 2) a second portion that extends into the inner surface of the body portion but does not extend through to the outer surface of the body portion,
wherein the second bone contacting region of the second arm is coplanar with the inner surface of the body portion.

12. The osteotomy guide of claim 11, wherein the body portion is an anterior body portion, the osteotomy guide further comprising:
an ascending leg having a first end that is attached to the anterior body portion, and a free end that is offset from the first end along the ascending direction, the ascending leg defining the second ascending guide surface.

13. The osteotomy guide of claim 11, wherein the ascending cutting path extends into the osteotomy guide along a descending direction, opposite the ascending direction, such that a proximal end of the ascending cutting path is open, and a distal end of the ascending cutting path is closed.

14. The osteotomy guide of claim 11, comprising:
an anterior body portion; and
a transverse leg having a first end that is attached to the anterior body portion, and a free end that is offset from the first end along the posterior direction, the transverse leg defining the second transverse guide surface.

15. The osteotomy guide of claim 11, wherein the transverse cutting path extends into the osteotomy guide along an anterior direction, opposite the posterior direction, such that a posterior end of the transverse cutting path is open, and an anterior end of the transverse cutting path is closed.

16. The osteotomy guide of claim 11, wherein the inner surface comprises:
an anterior bone contacting region that is defined by the anterior body portion and extends between proximal bone contacting region and distal bone contacting region, wherein the second portion of the gap terminates at the anterior bone contacting region.

17. The osteotomy guide of claim 16, wherein the gap extends into the posterior end and terminates at the anterior bone contacting region.

18. The osteotomy guide of claim 16, comprising:
an anterior body portion, wherein
the first arm is a proximal arm that extends from the anterior body portion along a posterior direction; and
the second arm is a distal arm that extends from the anterior body portion along the posterior direction.

19. The osteotomy guide of claim 11, wherein the transverse cutting path is elongate along a transverse direction, wherein the transverse cutting path intersects the ascending cutting path, and the ascending direction and the transverse direction define an obtuse angle as measured from one of the first and second ascending guide surfaces to one of the first and second transverse guide surfaces.

20. The osteotomy guide of claim 11, wherein the ascending groove defines an ascending plane that extends along the ascending direction and a direction that separates the inner and outer surfaces, and the ascending plane is offset in its entirety from the gap.

* * * * *